United States Patent
Mizuno et al.

(10) Patent No.: US 8,778,154 B2
(45) Date of Patent: Jul. 15, 2014

(54) METHOD OF MEASURING MICROPARTICLES HAVING NUCLEIC ACID AND APPARATUS THEREFOR

(75) Inventors: Akira Mizuno, Toyohashi (JP);
Kazunori Takashima, Toyohashi (JP);
Hachiro Yasuda, Toyohashi (JP);
Masudur Rahman, Toyohashi (JP)

(73) Assignee: Toyohashi University of Technology, Toyohashi-Shi (JP)

( * ) Notice: Subject to any disclaimer, the term of this patent is extended or adjusted under 35 U.S.C. 154(b) by 543 days.

(21) Appl. No.: 12/640,509

(22) Filed: Dec. 17, 2009

(65) Prior Publication Data
US 2010/0089754 A1     Apr. 15, 2010

Related U.S. Application Data

(63) Continuation of application No. PCT/JP2008/061210, filed on Jun. 19, 2008.

(30) Foreign Application Priority Data

Jun. 20, 2007 (JP) ................................. 2007-162261

(51) Int. Cl.
*B01D 57/02* (2006.01)
*B01D 59/42* (2006.01)
*C25B 7/00* (2006.01)

(52) U.S. Cl.
USPC ........... 204/450; 204/456; 204/462; 204/600; 204/606; 435/173.1; 435/173.4; 435/173.7; 435/173.9

(58) Field of Classification Search
USPC ............. 435/6.1, 173.1–173.9; 204/601–604, 204/450, 456, 462–464, 466, 606
See application file for complete search history.

(56) References Cited

U.S. PATENT DOCUMENTS

| | | | |
|---|---|---|---|
| 5,112,736 A * | 5/1992 | Caldwell et al. | 435/6.12 |
| 5,989,824 A * | 11/1999 | Birmingham et al. | 435/6.12 |
| 2008/0190219 A1 | 8/2008 | Jensen et al. | |
| 2008/0220414 A1 | 9/2008 | Jensen et al. | |

FOREIGN PATENT DOCUMENTS

| | | |
|---|---|---|
| EP | 0 402 997 A2 | 12/1990 |
| JP | 03-033656 A1 | 2/1991 |

(Continued)

OTHER PUBLICATIONS

R. F. Grossman and W. A. Beasley, Effects of Corona Discharge upon Polyethylen, Journal of Applied Polymer Science, II, 5, pp. 163-165 (1959).*

(Continued)

*Primary Examiner* — Luan Van
*Assistant Examiner* — Maris R Kessel
(74) *Attorney, Agent, or Firm* — Burr & Brown, PLLC

(57) ABSTRACT

To provide a system by which evaluation of circumstances of contamination by microparticles having nucleic acid can be performed rapidly and accurately. The theme is achieved by a system for measuring microparticles that includes: (1) a microparticle adhesion step of adhering the microparticles having nucleic acid to a microparticle adhesion member; (2) a membrane breakage step of breaking membranes of the adhered microparticles by electrical discharge; (3) an electrophoresis step of electrophoresing the microparticles in a thickness direction of a gel to make the nucleic acid in the microparticles migrate from a negative electrode side toward a positive electrode side and adhere the nucleic acid on a surface of a nucleic acid detection member; and (4) a nucleic acid measurement step of fluorescently staining the surface of the nucleic acid detection member to measure a concentration of the nucleic acid.

7 Claims, 8 Drawing Sheets

(56) References Cited

FOREIGN PATENT DOCUMENTS

| JP | 06-277060 | A1 | 10/1994 |
|----|-----------|----|---------|
| JP | 2003-200400 | A1 | 7/2003 |
| WO | 2005/083426 | A2 | 9/2005 |
| WO | 2005/083391 | A1 | 9/2009 |

OTHER PUBLICATIONS

Y. Klenko, V. Scholtz, Influence of a Point-to-Plane DC Negative Corona Discharge on Gel Surfaces, Acta Polytechnica, vol. 43, No. 4, pp. 27-29 (2008).*

User Manual, Hoefer SE 400/SE41 (2012).*

U. Yanagi, "*Behavior of Bio-Aerosol in Office Buildings and Methods of Control*," Green Technology, vol. 17, No. 5, 2007, pp. 44-47.

Sumiyo Ishimatsu, "*Capture and Detection of Airborne Microorganism Particles*," Green Technology, vol. 17, No. 5, 2007, pp. 48-51.

Kosuke Morikawa et al., "*Visualization of Individual DNA Molecules in Solution by Light Microscopy, DAPI Staining Method*," Communication, J. Biochem. vol. 89, No. 2, 1981, pp. 693-696.

A. Bensimon et al., "*Alignment and Sensitive Detection of DNA by a Moving Interface*," Science, vol. 265 (5181), Sep. 30, 1994, pp. 2096-2098.

* cited by examiner

Without discharge     After discharge

Cells not subject to discharge

Cells subject to discharge

Mixture of samples before and after discharge

METHOD OF MEASURING MICROPARTICLES HAVING NUCLEIC ACID AND APPARATUS THEREFOR

FIELD OF THE INVENTION

The present invention relates to a method and an apparatus related to measurement of microparticles having nucleic acid for ascertaining circumstances of contamination by microorganisms, etc., of air, wall surfaces, and floors of hospitals and food factories or utensils and clothing used for surgery and food manufacturing.

BACKGROUND OF THE INVENTION

From before, there have been needs to examine circumstances of contamination by microorganisms in air and on wall surfaces and floor surfaces of hospitals, food factories, and other locations where particular attention must be paid to sanitation as well as to examine circumstances of contamination by microorganisms of utensils and clothing used for surgery and food manufacturing (Non-Patent Document 1). In a conventional method, a sample is coated as a solution onto a culture medium or a membrane having a plurality of cells fixed thereon, formation of colonies by a microorganism or loss of the cells spread in the form of the membrane due to a virus is made to occur, and evaluation is performed by counting the number of colonies or number of loss (Non-Patent Document 2).

Meanwhile, by advances made in single-molecule DNA manipulation and measurement arts through progress of technical development in recent years, it has become possible to make clear observations by fluorescently staining of single-molecule DNA (Non-Patent Document 3). Using this art, it is becoming possible to take out a DNA molecule from a cell, extend and fix the DNA molecule on a substrate, and adhere a fluorescently stained restriction enzyme to the extended and fixed DNA to prepare a restriction map using a fluorescence microscope (Patent Document 1 and Non-Patent Document 4).

Patent Document 1: Japanese Published Unexamined Patent Application No. 2003-200400
Non-Patent Document 1: U Yanagi: "Behavior of bio-aerosol in office buildings and methods of control," Green Technology, vol. 17, No. 5, 44-47, 2007
Non-Patent Document 2: Sumiyo Ishimatsu: "Capture and detection of airborne microorganism particles," Green Technology, vol. 17, No. 5, 48-51, 2007
Non-Patent Document 3: Morikawa K., and Yanagida M., J. Biochem., 89, pp. 693-696, 1981
Non-Patent Document: A. Bensimon, A. Simon, A. Chiffaudel, V. Croquette, F. Heslot, D. Bensimon, "Alignment and sensitive detection of DNA by a moving interface," Science, Vol. 265(5181), pp. 2096-2098, 1994

SUMMARY OF THE INVENTION

With the present invention, a method of visualizing a single molecule is applied to detection of particles having nucleic acid to rapidly and accurately count microorganisms in an environment.

Conventionally, evaluation of circumstances of contamination by microorganisms in an environment is carried out by colony formation or cell loss by culturing. However, a time of several days is required to culture cells or to infect cells with a virus to cause cell loss. Even with a method of using a fluorescent dye to stain and observe DNA in a cell, a cell membrane is not high in dye permeability and thus a staining process time of not less than approximately ten hours is required (Non-Patent Document 2). Frequently in this process, organelles inside the cell are fluorescently stained at the same time, and this has been a cause of error. When fluorescent staining is performed upon breaking the cell membrane to reduce the processing time, biopolymers besides the nucleic acid become stained and this becomes a cause of error.

As a result of repeating diligent research in view of the above circumstances, the present inventor has come to complete the following invention.

A method of measuring microparticles having nucleic acid according to a first aspect of the present invention includes: (1) a microparticle adhesion step of adhering the microparticles having nucleic acid to a microparticle adhesion member; (2) a membrane breakage step of breaking membranes of the adhered microparticles by electrical discharge; (3) an electrophoresis step of electrophoresing the microparticles in a thickness direction of a gel to make the nucleic acid in the microparticles migrate from a negative electrode side toward a positive electrode side and adhere the nucleic acid on a surface of a nucleic acid detection member; and (4) a nucleic acid measurement step of fluorescently staining the surface of the nucleic acid detection member to measure a concentration of the nucleic acid.

Preferably, in the present invention, in the microparticle adhesion step, the microparticle adhesion member is placed on a surface at a smooth electrode side of a corona discharge electrode and microparticles having nucleic acid that are suspended in air are adhered to the surface of the microparticle adhesion member.

Also, preferably in the membrane breakage step, an electrode system, in which an insulating plate is inserted between mutually opposing electrodes, is used, the microparticle adhesion member is inserted in a gap between the electrodes, and the membranes of the microparticles are broken by applying an alternating voltage across the electrodes.

Also, preferably, the surface of the nucleic acid detection member to which the nucleic acid is electrophoresed has a positive surface charge.

A system for measuring microparticles having nucleic acid according to a second aspect of the present invention includes: a microparticle adhesion member on which the microparticles having nucleic acid are adhered; a microparticle adhesion apparatus making the microparticles having nucleic acid adhere to a surface of the microparticle adhesion member; a membrane breakage apparatus using electrical discharge to break membranes of the microparticles that are adhered to the microparticle adhesion member; a nucleic acid detection member in turn including a tape, including a charge neutralizer, and a gel, disposed on one surface side of the tape; an electrophoresis apparatus electrophoresing the nucleic acid, adhered to the surface of the microparticle adhesion member, through the gel of the nucleic acid detection member to make the nucleic acid migrate to the tape side; and a nucleic acid detection apparatus detecting the nucleic acid on the tape surface in a state where the gel of the nucleic acid detection member is removed.

Preferably, in the present invention, the microparticle adhesion apparatus includes: a corona discharge electrode having a needle electrode and a flat plate electrode; and makes the microparticles adhere to the surface with the microparticle adhesion member being set on the flat plate electrode.

Also preferably, the membrane breakage apparatus includes: mutually opposing electrodes; an insulating plate inserted between the electrodes; and a member mounting space into which the microparticle adhesion member is inserted; and breaks the membranes by applying an alternating voltage across the electrodes.

Also preferably, the tape of the nucleic acid detection member has a positive surface charge.

Also preferably, the nucleic acid detection member serves in common as the microparticle adhesion member, and a microparticle membrane breaking operation is performed in the state where the microparticles having nucleic acid are adhered to the surface of the gel.

The nucleic acid may be either RNA or DNA. The nucleic acid may be either single-stranded or double-strand and may be cyclic or linear.

The microparticles having nucleic acid refer to those having nucleic acid and include microorganisms (including bacteria, fungi, yeasts, molds, etc.), viruses, viroids, etc.

To examine a concentration of bacteria, virus particles, or other microparticles having nucleic acid, the nucleic acid (DNA, RNA) contained in the inside must be taken out by efficiently breaking a cell membrane or a protein envelope and just the nucleic acid must be fluorescently stained and counted. In the present invention, electrical discharge is used to rapidly take out the nucleic acid from the bacteria or virus. In particular, by performing discharge breakage using the electrode system with the insulating plate inserted between the mutually opposing electrodes, the cells can be destroyed within a few minutes to take out the nucleic acid. This is an extremely short time in comparison to an enzyme reaction, etc., that breaks the cell membrane.

An object of the present invention is to perform concentration measurement of microparticles having nucleic acid in a short time. By using the discharge breakage, the microparticles adhered to the microparticle adhesion member can be broken on the spot. A considerable amount of sample is required to perform a nucleic acid extraction operation upon transferring the microparticles having nucleic acid once into solution as is done conventionally. A microparticle capturing operation that takes a long time is thus required to collect a large amount of the sample, and rapid concentration measurement thus could not be performed.

On the other hand, by the invention of the present application, the nucleic acid that diffuses to the surface of the microparticle adhesion member from the cell or virus that has been broken at the surface is separated from histones and other proteins by a surfactant or other charge neutralizer coated on the microparticle adhesion member. That is, after taking out the nucleic acid from the microparticles by the discharge breakage, the nucleic acid is distinguished from other component molecules by fractionation by electrophoresis. To reduce the time for electrophoresis, the migration distance must be reduced as much as possible. In the nucleic acid detection member of the present invention, the membrane having the thin gel layer on the surface of the tape is used to electrophorese the nucleic acid in the thickness direction of the gel layer and thereby fractionate the nucleic acid from other biopolymers. The nucleic acid that has been electrophoresed to the tape through the gel layer adheres to the tape surface. In this state, the nucleic acid has a negative charge, and thus by using the tape that is made to have the surface charge of positive polarity, the separated nucleic acid can be adhered and held reliably on the tape.

After performing electrophoresis, the gel is peeled off from the tape. The nucleic acid that is adhered on the tape is then fluorescently stained. For the fluorescent staining, YOYO, ethidium bromide, DAPI, or other general dye for fluorescently staining DNA or RNA may be used. To hold the nucleic acid on the surface reliably after electrophoresis, a material having a positive surface charge is preferably used in the tape. Although the number of the nucleic acid extracted from a single microparticle with nucleic acid is plural in many cases, the distribution range thereof is generally within several times a diameter of the microparticle, and thus by identifying this group by image processing, counting as the nucleic acid group of one microparticle can be performed.

With airborne microparticles, corona discharge is used to make the microparticles adhere to the surface of the microparticle adhesion member. The microparticles can thereby be electrically collected on the membrane surface at high efficiency. Also, where necessary, the counting precision of the microparticles can be improved by adjusting the corona discharge voltage or the flow rate of the air containing the microparticles that are introduced into the corona discharge field and thereby controlling the adhesion density of the microparticles having nucleic acid.

Also, by configuring the microparticle adhesion member and the nucleic acid detection member as a member in common by configuring the nucleic acid detection member from the tape and the gel disposed on one surface side of the tape, the microparticle adhesion step, the membrane breakage step, the electrophoresis step, and the nucleic acid measurement step can be performed while supplying the nucleic acid detection member in a continuous manner, thereby realizing an extremely rapid measurement system.

DETAILED DESCRIPTION OF THE INVENTION

Figure 1:
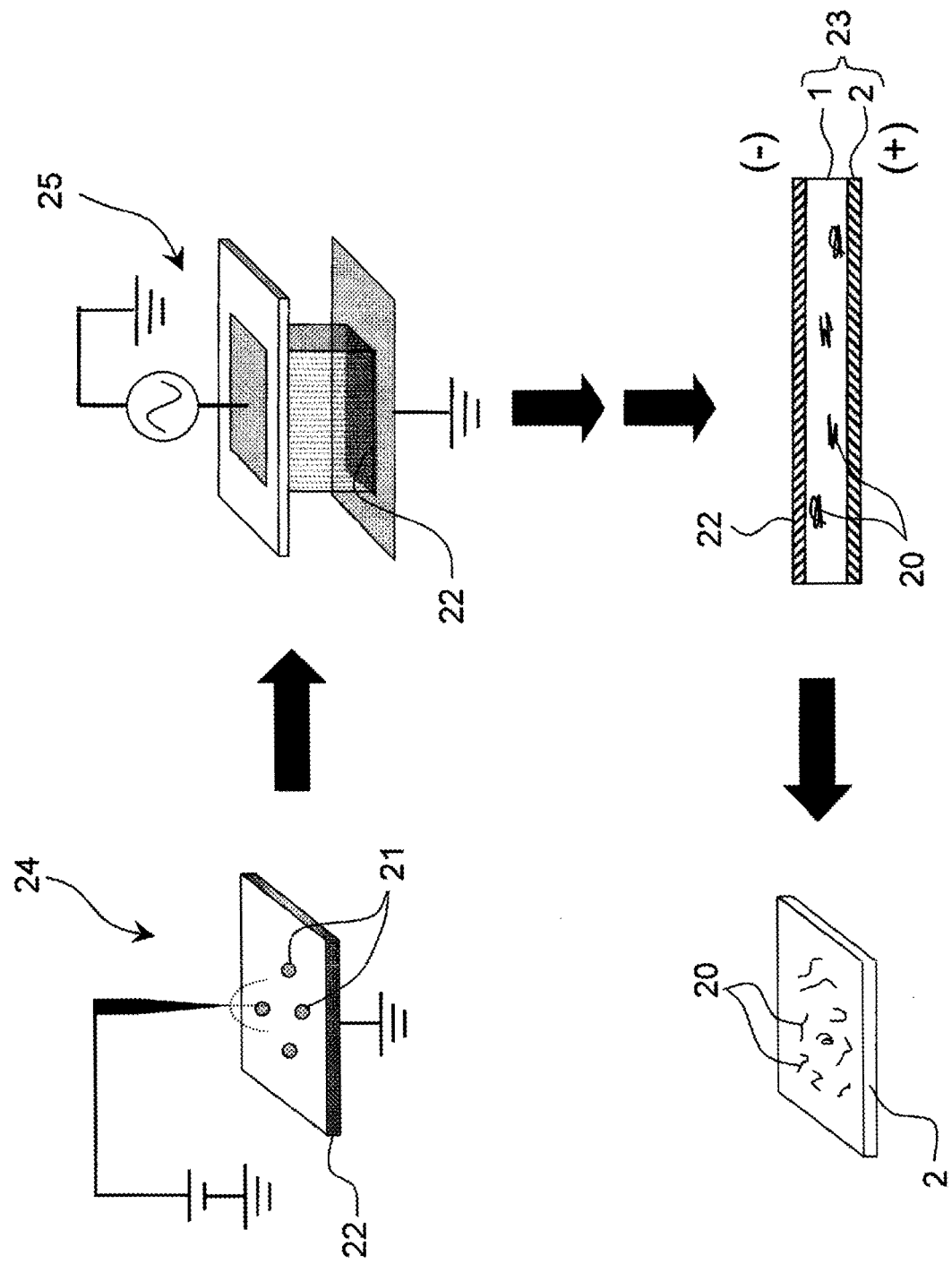
FIG. 1 is a process diagram for describing an embodiment in outline.

FIG. 1 is a process diagram for describing an embodiment in outline. In this process diagram, the microparticle adhesion member 22 and the nucleic acid detection member 23 are configured as different members. The microparticles 21 having nucleic acid 20 proceed through the steps according to the arrows from an upper left side of the figure, and by proceeding through the steps at an upper right side, a lower right side, and a lower left side, the nucleic acid 20 is measured.

First, in a microparticle adhesion step at the upper left, the microparticles 21 having nucleic acid are adhered to the surface of the microparticle adhesion member 22. The microparticle adhesion member 22, on which the microparticles 21 are thus adhered, proceeds to a subsequent membrane breakage step (upper right of the figure).

With the microparticles, with which the membranes have been broken, an electrophoresis step of using a gel 1 and electrophoresing in a thickness direction of the gel is then performed to make the nucleic acid 20 migrate from a negative electrode side toward a positive electrode side. The nucleic acid 20 thus migrates to a surface of a tape 2 of a nucleic acid detection member 23 (lower right of the figure).

Finally, the gel 1 on the nucleic acid detection member 23 is removed, the nucleic acid 20 adhered on the surface of the tape 2 is fluorescently stained, and a concentration of the nucleic acid 20 is measured (nucleic acid measuring step).

Figure 2:
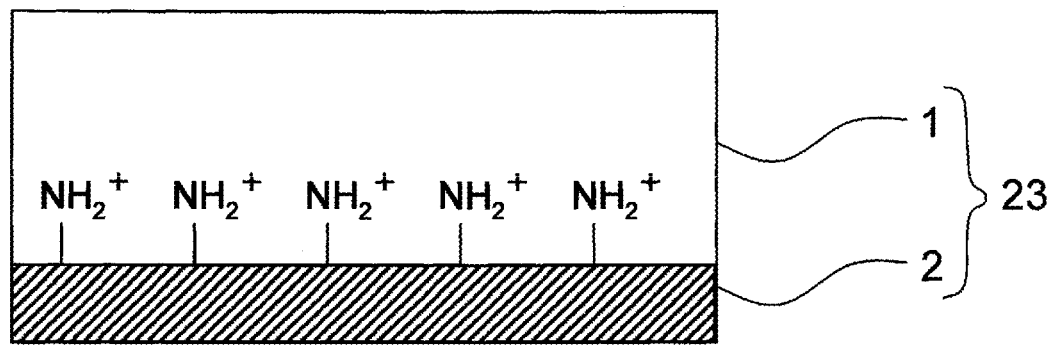
FIG. 2 is a sectional side view of a nucleic acid detection member for capturing microparticles with nucleic acid.

Details of the respective steps shall now be described. FIG. 2 is a sectional side view of the nucleic acid detection member 23 for electrophoresing the microparticles 21. The nucleic acid detection member 23 has, as a substrate, the plastic tape 2 formed from a non-woven fabric that is surface treated with an amino group ($NH_2^+$) to have a surface charge of positive polarity, and has on the surface thereof a membrane formed by coating the agarose gel 1 to a thickness of not less than approximately 1 mm. The gel 1 is used to electrophorese the microparticles 21 having nucleic acid. The nucleic acid detection member 23 that is configured as a tape-like membrane is stored in a cartridge and can be supplied in a continuous manner. For example, the tape may be approximately 1 mm to 5 mm in width. The nucleic acid detection member 23 can be used in common as the microparticle adhesion member 22. That is, after adhering the microparticles 21 on the surface of the agarose gel 1, the membranes of the microparticles 21 are broken, and then electrophoresis is performed to make the nucleic acid 20 migrate in the direction of the tape 2 and adhere to the surface of the tape.

Figure 3:
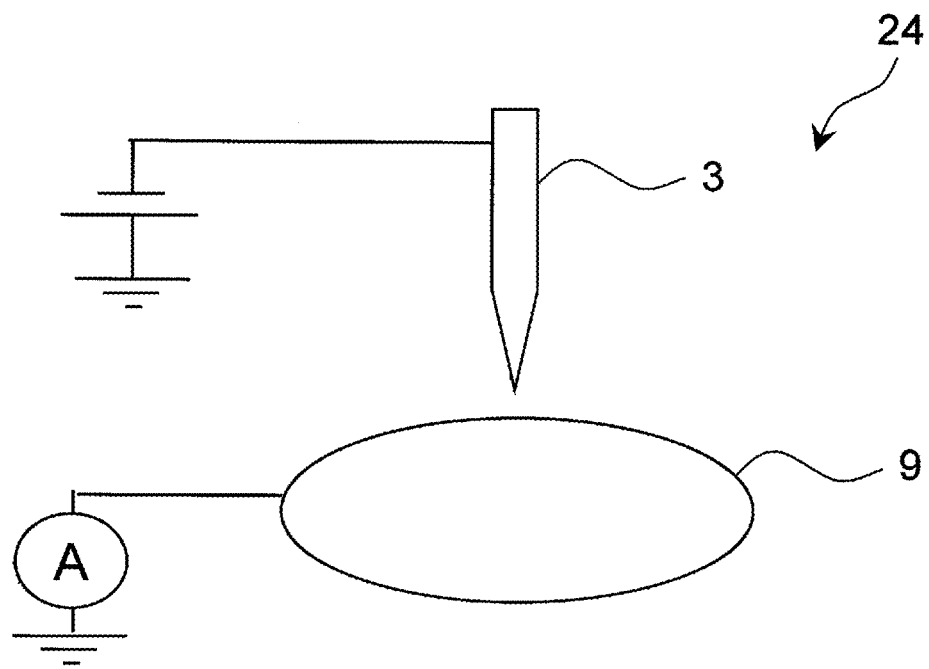
FIG. 3 is a schematic view of a corona discharge apparatus.

A corona discharge apparatus (microparticle adhesion apparatus) 24, shown in FIG. 3, can be used to make microparticles having nucleic acid that are suspended in air adhere to a tape-like membrane. The corona discharge apparatus 24 includes a needle-like high-voltage electrode 3 and a flat plate ground electrode 9. A distance between the electrodes 3 and 9 is set to an interval of approximately 5 mm to 10 mm, and the microparticle adhesion member 22 is supplied to a surface of the flat plate ground electrode 9.

To use the tape-like nucleic acid detection member 23 to adhere microparticles having nucleic acid that are adhered to a wall or clothing, etc., the nucleic acid detection member 23 is drawn out from the cartridge and the surface of the gel 1 is directly contacted with the wall or clothing, etc. Or, the membrane-like microparticle adhesion member 22 (or the nucleic acid detection member 23 serving in common as the microparticle adhesion member 22) of a diameter of approximately several mm may be prepared separately and put in contact with the wall or clothing, etc., and the subsequent processes of nucleic acid extraction, fluorescence staining, etc., may be performed thereafter.

Figure 4:
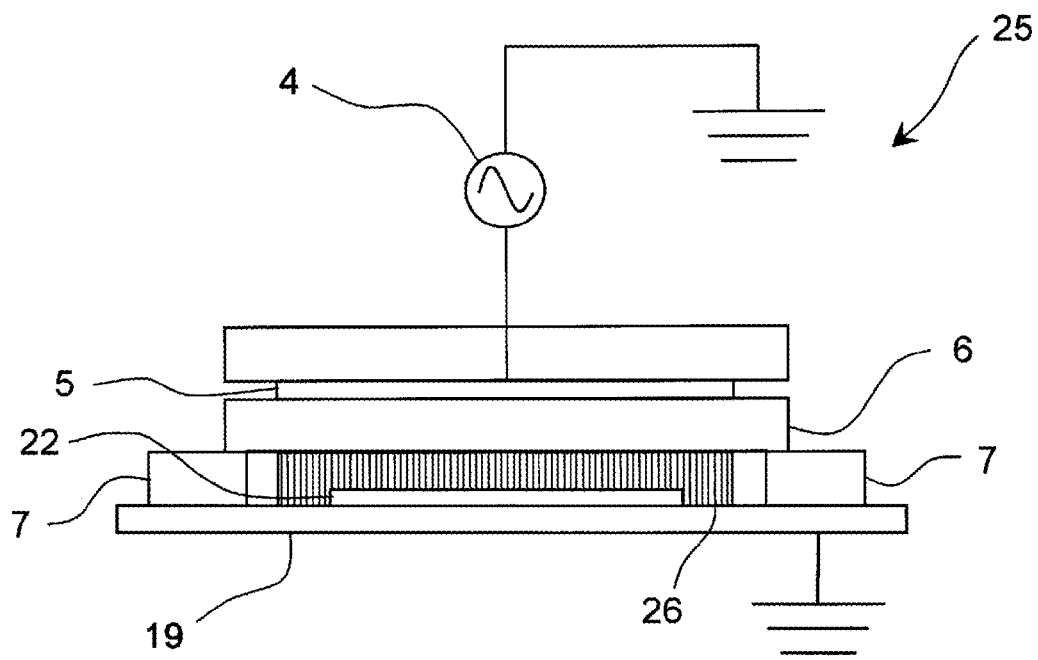
FIG. 4 is a schematic view of a membrane breakage apparatus for breaking membranes of microparticles.

FIG. 4 shows a membrane breakage apparatus 25 that can be used in the membrane breakage step. The membrane breakage apparatus 25 includes mutually opposing silent discharge electrodes 5 and 19, an insulating plate 6 inserted between the two electrodes, and a member mounting space 26 into which the microparticle adhesion member 22 is inserted. The two discharge electrodes 5 and 19 are configured as parallel plate electrodes, and by disposing the insulating plate 6 at the electrode at one side, a gap of the member mounting space 26 is set to not more than approximately 2 mm. The electrode 5 at the upper side is configured from a stainless-steel mesh, and the electrode 19 at the lower side is the ground electrode. A high-voltage alternating power supply 4 is connected to the electrode 5. Also, a spacer 7 of predetermined thickness is sandwiched between the insulating plate 6 and the electrode 9. An alternating voltage, for example, of 30 kHz and approximately 10 kV is applied to generate a silent discharge.

After the microparticles 21 having the nucleic acid 20 are adhered to the microparticle adhesion member 22, the microparticle adhesion member 22 is inserted into the member mounting space 26, and the membranes of the microparticles 21 are broken by the silent discharge.

Figure 5:
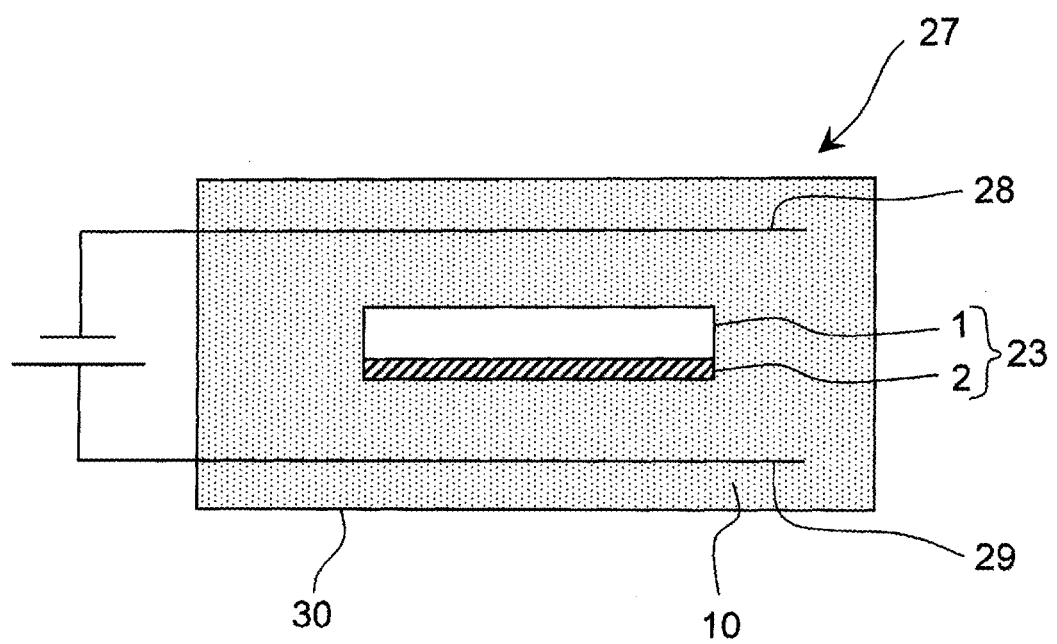
FIG. 5 is a schematic view of an electrophoresis apparatus for making nucleic acid migrate from a gel surface to a tape.

Subsequently, the nucleic acid 20 is extracted by adding SDS or other surfactant to the surfaces of the membranes of the broken microparticles 21 having the nucleic acid 20 that are adhered to the surface of the microparticle adhesion member 22. Thereafter, an electrophoresis apparatus 27, shown in FIG. 5, is used to perform electrophoresis of the nucleic acid 20. The electrophoresis apparatus 27 includes a container 30, in which is placed an aqueous solution (electrolyte solution 10) that has conductivity, and a pair of positive and negative electrodes 28 and 29 disposed at a bottom surface and an upper surface of the container 30. The nucleic acid detection member 23 is inserted between the two electrodes 28 and 29 to perform electrophoresis of the nucleic acid 20. The electrophoresis is performed in the direction of thickness of the gel 1 with the gel 1 side of the nucleic acid detection member 23 being negative and the tape 2 side being positive, and the nucleic acid 20 is electrophoresed from the gel 1 surface to the tape 2. The time required for electrophoresis is normally about several minutes.

After performing the electrophoresis, the nucleic acid detection member 23 is removed from the electrophoresis apparatus 27, and the gel 1 is peeled off by a scraper to leave just the tape 2 on which the nucleic acid 20 is adhered. Thereafter, the tape 2 is passed through a container in which a fluorescent dye solution is placed to fluorescently stain the adhered nucleic acid 20.

Thereafter, excitation light is irradiated on the tape 2 to make fluorescence be emitted, and the nucleic acid 20 that emits fluorescence is counted.

EXAMPLES

Capture of Microparticles Having Nucleic Acid by Corona Discharge

Figure 6:
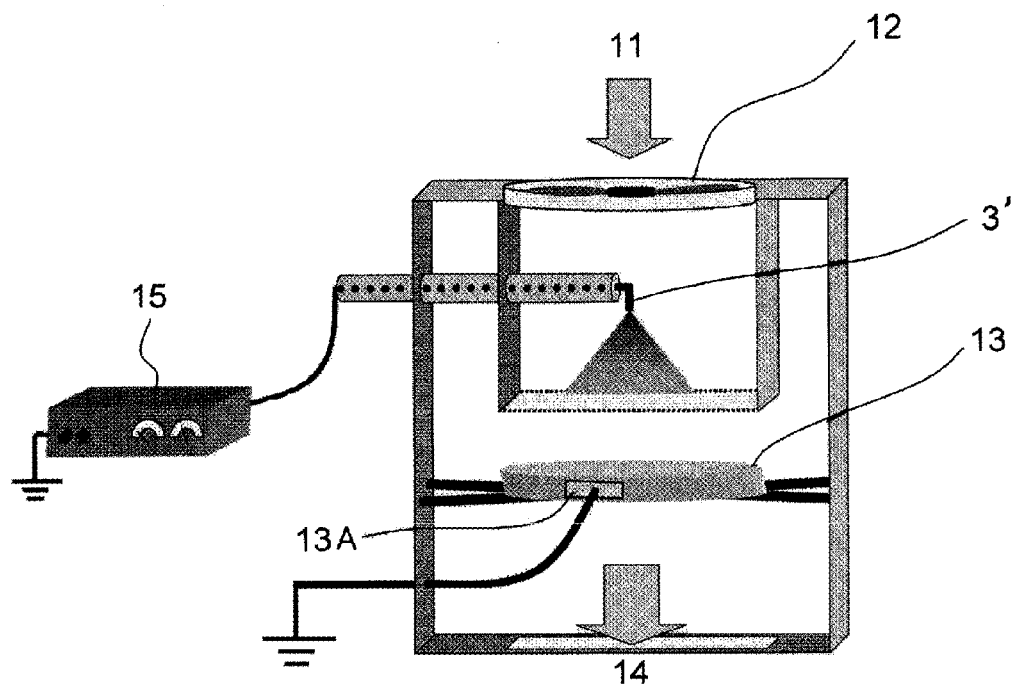
FIG. 6 is a schematic view of a microparticle adhesion apparatus for capturing microparticles having nucleic acid by corona discharge.

A microparticle adhesion apparatus including a corona discharge electrode, shown in FIG. 6, was used to capture bacteria suspended in air. The apparatus includes a needle-like, high-voltage electrode 3' for corona discharge, a culture medium 13 serving as a flat plate ground electrode (collecting electrode), and a high-voltage DC power supply 15. The symbol 13A indicates an electrode for grounding the culture medium 13. A fan 12 is disposed at an upper surface side of the apparatus. By driving the fan 12, air in a room is introduced from the upper surface side (symbol 11) and discharged from a lower surface side (symbol 14). When the air passes between the two electrodes 3' and 13, the microparticles with nucleic acid are captured by the culture medium 13.

Figure 7:
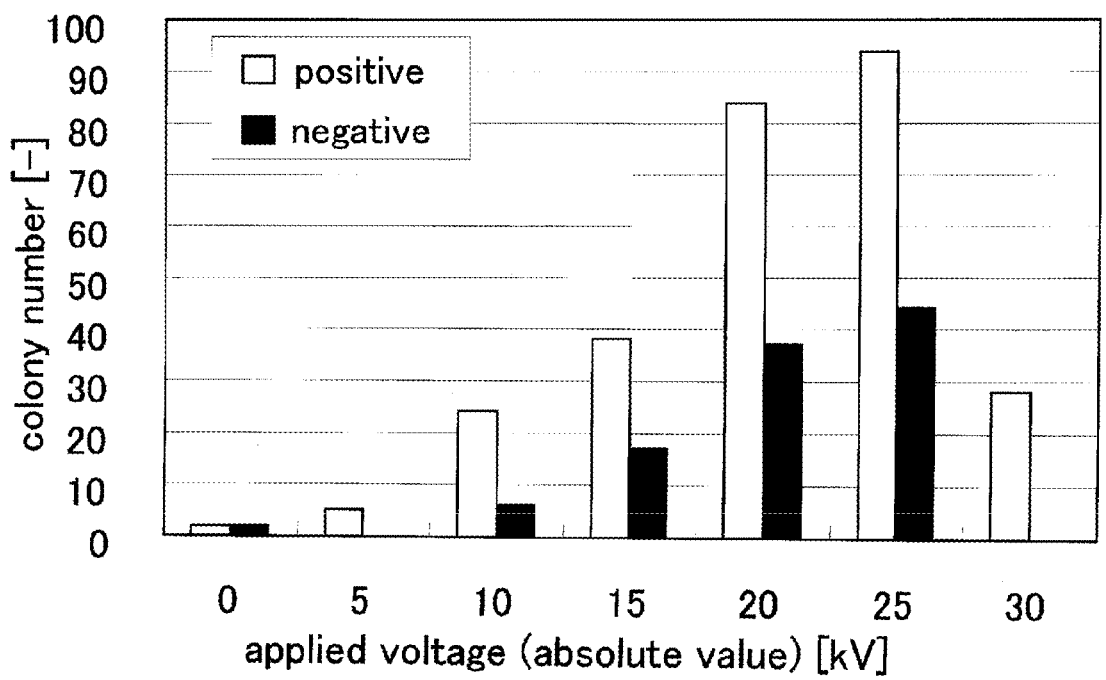
FIG. 7 is a graph of measurement results of number of live bacteria included among microparticles captured by corona discharge. In the figure, outline bars indicate results in a case where a culture medium is set to a positive polarity and solid bars indicate results in a case where the culture medium is set to a negative polarity.

FIG. 7 shows counting results of number of colonies resulting from capturing microparticles using the apparatus. Indoor air was fed at a rate of 18 liters per second to the lower side by the fan 12, and corona discharge was generated across the silver needle electrode 3' and the culture medium 13. The numbers of colonies observed were counted upon subjecting the culture medium 13 to culturing for 2 days after performing corona discharge for 10 minutes with the culture medium 13 side being set to positive or negative polarity and the voltage being varied from 0 kV to 30 kV.

As a result, it was confirmed that (1) in both cases of using positive polarity and negative polarity, the number of bacteria captured is increased by not less than 10 times by the corona discharge for ten minutes (22 times in the case of negative polarity and 47 times in the case of positive polarity), and that (2) when corona discharge of positive polarity is used, a capture efficiency of live bacteria is improved in comparison to the case where corona discharge of negative polarity is used. It is considered that the number of bacteria colonies was greater when corona discharge from the positive electrode was performed because generation of ozone, which is harmful to bacteria, is suppressed in the case of atmospheric corona discharge at the silver positive electrode.

Breakage of Bacteria by Silent Discharge

Figure 8:
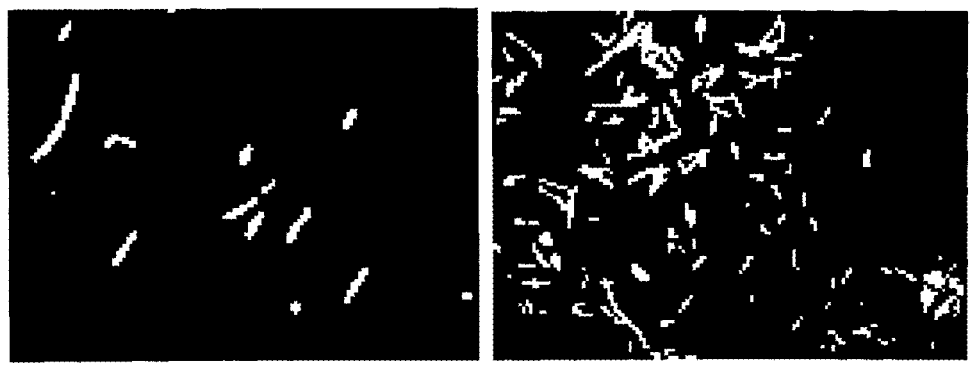
FIG. 8 shows photographs of results of performing a silent discharge process on *Escherichia coli* containing the fluorescent protein GFP in the bodies thereof. It can be understood that by applying the discharge process, the membranes of the *E. coli* are broken so that the GFP contained inside the cells diffuse and the fluorescent intensity is thereby attenuated largely.
Figure 8:
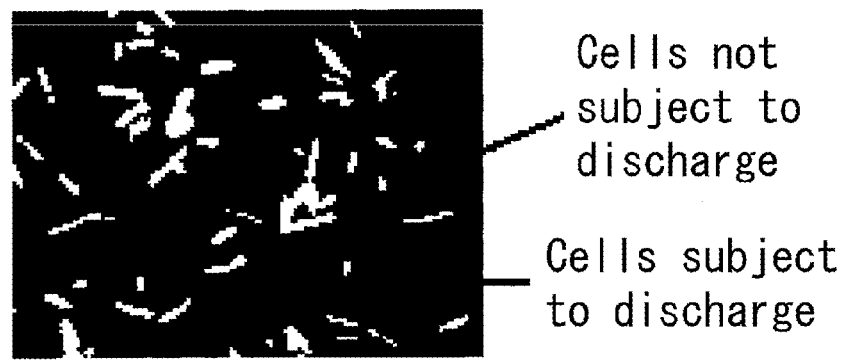
Figure 9:
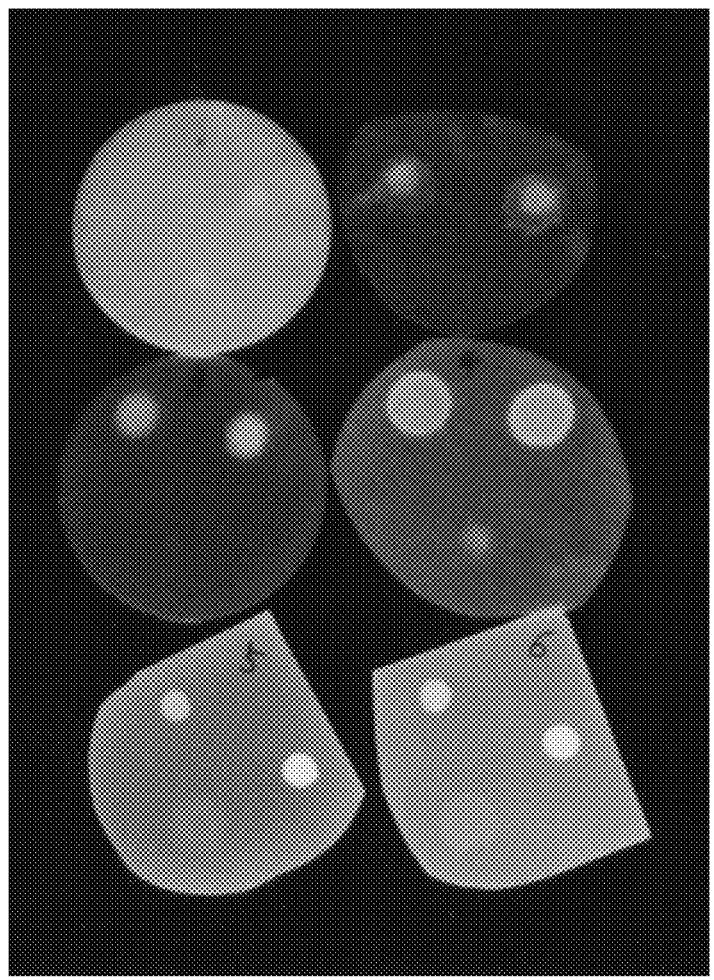
FIG. 9 is a fluorescence photograph of DNA coated on various filter surfaces.
Figure 10:
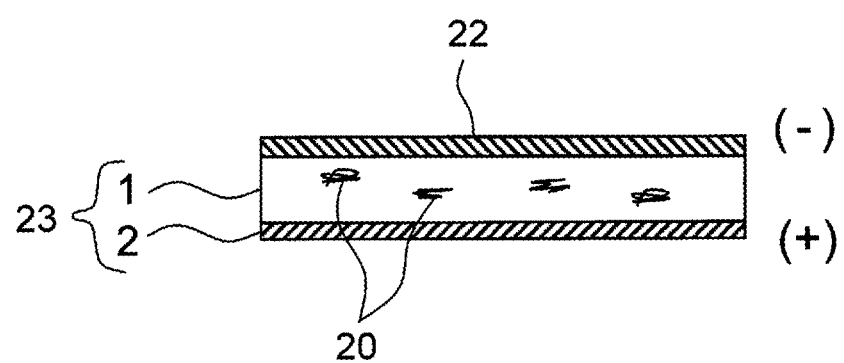
FIG. 10 is a schematic sectional side view of a state where a microparticle adhesion member and a nucleic acid detection member are adhered together closely and DNA is electrophoresed.
Figure 11:
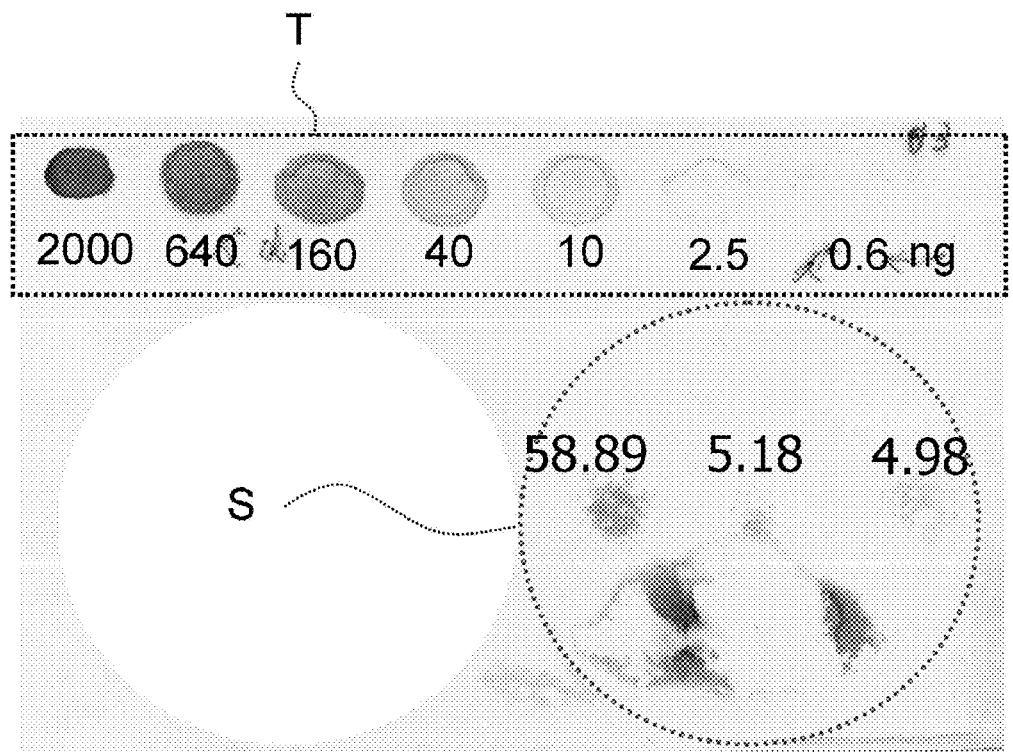
FIG. 11 is a photograph of DNA transferred onto a tape of the nucleic acid detection member after the electrophoresis process. A dotted line rectangle T indicates a region onto which reference amounts of DNA were dropped, and a dotted circle S indicates a region of the electrophoresed DNA. Numerical values inside T and S indicate DNA amounts.
Figure 12:
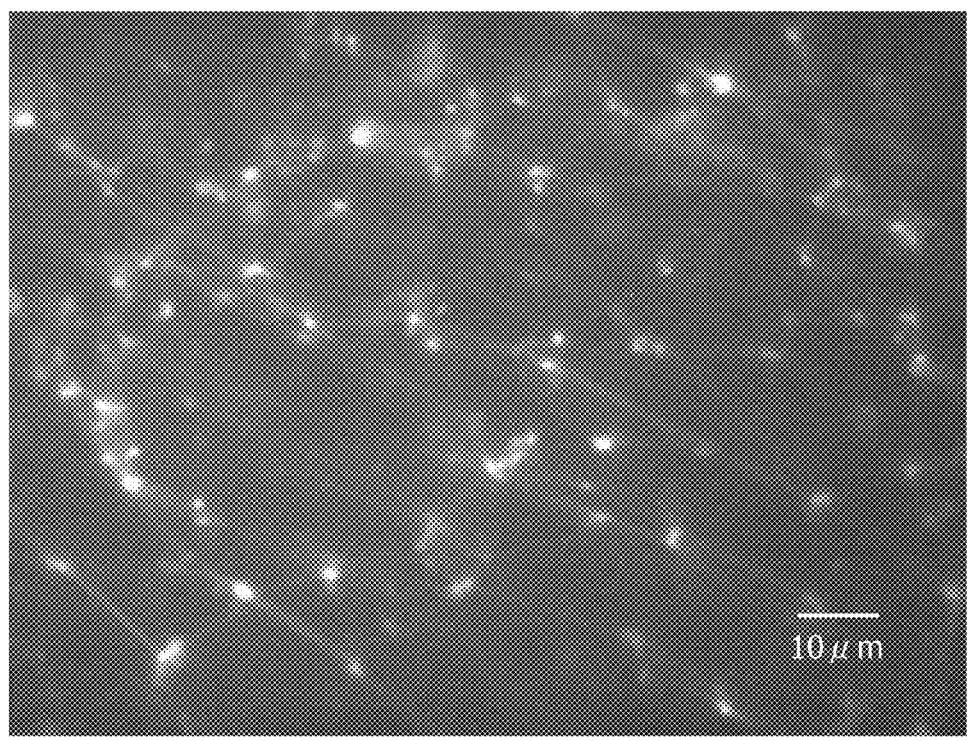
FIG. 12 is a fluorescence micrograph image of DNA adhered to a filter.
Figure 13:
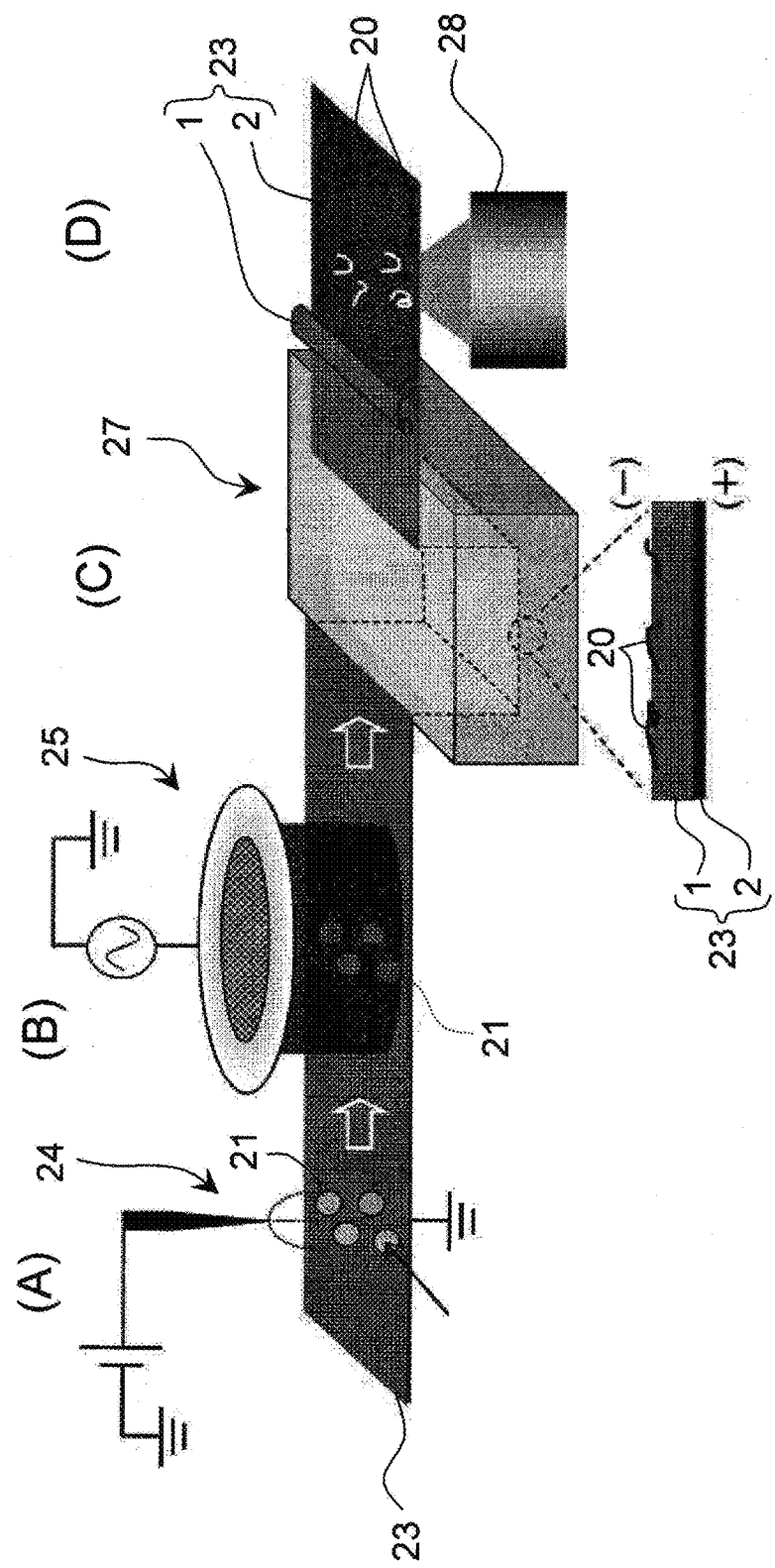
FIG. 13 is an outline diagram of a counting system for microparticles having nucleic acid.

FIG. 8 shows photographs of *Escherichia coli* after breakage of membranes. For fluorescence to be generated, the *E. coli* used has introduced therein a gene that produces the jellyfish-derived fluorescent protein GFP. The microparticle adhesion member 22, having the *E. coli* coated thereon, was set in the membrane breakage apparatus 25 including the silent discharge electrodes 5 and 19 shown in FIG. 4, and an alternating voltage of 30 kHz and 25 kVpp was applied. When the cell membranes of *E. coli* are broken, the GFP contained in the cells diffuses, and the breakage can thus be confirmed by a large attenuation of the fluorescence intensity. Even from a fluorescence photograph of a sample in which *E. coli* not subject to the silent discharge process and *E. coli* broken by the silent discharge process are mixed, was confirmed that the fluorescence intensity is attenuated largely by the silent discharge process. Although an enzyme reaction is normally used for breaking the cell membranes of *E. coli*, this process requires several hours, and thus the breakage of bacteria by silent discharge has a characteristic that it can be performed in an extremely short time.

Electrophoresis of DNA

FIG. 9 is a fluorescence photograph of a case where a DNA molecule group is coated on the surface of the microparticle adhesion member 22. As shown schematically in FIG. 10, electrophoresis of DNA was performed by the electrophoresis apparatus 27 upon putting the nucleic acid detection member 23 in close contact with the surface side of the microparticle adhesion member 22 on which the DNA molecules were coated (lower surface side in the figure).

FIG. 11 shows results of fluorescently staining the tape 2 of the nucleic acid detection member 23 after the electrophoresis. By measurement of the DNA amount by staining, it was confirmed that approximately 30 to 50% of the DNA molecules migrated from the microparticle adhesion member 22 and became adhered to the tape 2 by the electrophoresis. FIG. 12 is a fluorescence micrograph image of the DNA adhered to the tape 2. It was thus demonstrated that individual DNA molecules can be identified. The electrophoresis time is only a few minutes, and it was demonstrated that DNA can be sampled through the thin gel.

System for Counting Microparticles with Nucleic Acid

FIG. 13 shows, in outline, a counting system according to a present embodiment. This system has a configuration where the nucleic acid detection member 23 is used in common as the microparticle adhesion member. The nucleic acid detection member 23 is manufactured in a continuous, band-like manner and is subject to the microparticle adhesion step (A), the membrane breakage step (B), the electrophoresis step (C), and the nucleic acid measurement step (D) by moving at a predetermined speed from a left side to a right side of the figure.

That is, the nucleic acid detection member 23 passes through the corona discharge apparatus 24 with the gel 1 being faced upward. The microparticles 21 with the nucleic acid become adhered to the surface of the gel 1 in this process. When the nucleic acid detection member 23 then passes through the inside of the member mounting space 26 of the membrane breakage apparatus 25, the membranes of the microparticles 21 are broken by silent discharge.

When the nucleic acid detection member 23 then passes through the electrophoresis apparatus 27, the nucleic acid 20 migrates through the inside of the gel 1 as it is electrophoresed from the negative electrode side toward the positive electrode side and becomes adhered to the surface of the tape 2.

After passage through the electrophoresis apparatus 27, the gel 1 of the nucleic acid detection member 23 is peeled off, leaving just the tape 2, and thereafter, the nucleic acid 20 is measured by irradiation from the nucleic acid detection apparatus 28 that generates the excitation light.

Thus, by the present invention, it has become possible to perform from the capture of the microparticles 21 having the nucleic acid 20 to the breakage of the microparticles 21, extraction of the nucleic acid 20, the fixing of the nucleic acid to the tape 2 surface by electrophoresis, fluorescent staining, and counting within 10 minutes.

INDUSTRIAL APPLICABILITY

By the present invention, the evaluation of circumstances of contamination by microorganisms and viruses of air, wall surfaces, and floors of hospitals and food factories or utensils and clothing used for surgery and food manufacturing can be performed within 10 minutes, thereby enabling ascertainment of danger of infection or taking of measures necessary for preventing infection to be performed substantially at real time. and application to sanitation control is thus anticipated.

DESCRIPTION OF REFERENCE NUMERALS

1 agarose gel
2 plastic membrane with positive charge
3, 3' needle electrode
5 discharge electrode
6 insulating plate
9, 19 ground electrode
13 culture medium (flat plate ground electrode)
20 nucleic acid
21 microparticle
22 microparticle adhesion member

23 nucleic acid detection member
24 microparticle adhesion apparatus
25 membrane breakage apparatus
26 member mounting space
27 electrophoresis apparatus
28 nucleic acid detection apparatus

What is claimed is:

1. A method of measuring microparticles having nucleic acid comprising:

a microparticle adhesion step of adhering the microparticles having nucleic acid to a microparticle adhesion member, the microparticle adhesion member being a gel, the microparticle adhesion step comprising associating the gel with a corona discharge electrode, and adhering microparticles having nucleic acid that are suspended in air to the surface of the gel;

a membrane breakage step of breaking membranes of the microparticles having nucleic acid by electrical discharge on the gel;

an electrophoresis step of electrophoresing the microparticles having nucleic acid in a thickness direction of the gel, migrating the nucleic acid in the microparticles having nucleic acid from a negative electrode side toward a positive electrode side and adhering the nucleic acid on a surface of a nucleic acid detection member; and a nucleic acid measurement step of removing the gel from the nucleic acid detection member and fluorescently staining the surface of the nucleic acid detection member to measure a concentration of the nucleic acid.

2. The method of measuring microparticles having nucleic acid according to claim 1, wherein in the microparticle adhesion step, the gel is placed on a surface at a smooth electrode side of the corona discharge electrode.

3. The method of measuring microparticles having nucleic acid according to claim 1, wherein in the membrane breakage step, an electrode system, in which an insulating plate is inserted between mutually opposing electrodes, is used, the gel is inserted in a gap between the electrodes, and the membranes of the microparticles having nucleic acid are broken by applying an alternating voltage across the electrodes.

4. The method of measuring microparticles having nucleic acid according to claim 1, wherein the surface of the nucleic acid detection member to which the nucleic acid is electrophoresed has a positive surface charge.

5. The method of measuring microparticles having nucleic acid according to claim 2, wherein in the membrane breakage step, an electrode system, in which an insulating plate is inserted between mutually opposing electrodes, is used, the gel is inserted in a gap between the electrodes, and the membranes of the microparticles having nucleic acid are broken by applying an alternating voltage across the electrodes.

6. The method of measuring microparticles having nucleic acid according to claim 2, wherein the surface of the nucleic acid detection member to which the nucleic acid is electrophoresed has a positive surface charge.

7. The method of measuring microparticles having nucleic acid according to claim 3, wherein the surface of the nucleic acid detection member to which the nucleic acid is electrophoresed has a positive surface charge.

* * * * *